United States Patent [19]
Marinkovich

[11] 3,941,876
[45] Mar. 2, 1976

[54] IN VITRO METHOD FOR DETERMINING ALLERGIC HYPERSENSITIVITY
[75] Inventor: Vincent A. Marinkovich, Palo Alto, Calif.
[73] Assignee: GTE New Ventures Corporation, Del.
[22] Filed: Apr. 25, 1973
[21] Appl. No.: 354,881

[52] U.S. Cl.................. 424/1; 23/230 B; 424/8; 424/12; 424/91; 23/253 TP; 252/408
[51] Int. Cl.² ........................................ A61B 10/00
[58] Field of Search ............... 424/1, 8, 12, 91; 23/253 TP, 230 B

[56] References Cited
UNITED STATES PATENTS
| | | | |
|---|---|---|---|
| 3,443,903 | 5/1969 | Haack | 23/230 B |
| 3,549,328 | 12/1970 | Kilburn | 23/230 B |
| 3,838,012 | 9/1974 | Higgens | 23/230 B |

OTHER PUBLICATIONS
"Immunochemistry", Vol. 4, pp. 11–22 (1967).
"The Journal of Immunology", Vol. 99, pp. 849–858.
"Int. Rev. Cytol.", Vol. 5, p. 1 (1956).
"Nature", Vol. 194, p. 495 (1962).

Primary Examiner—Benjamin R. Padgett
Assistant Examiner—Donald P. Walsh

[57] ABSTRACT

Allergic hypersensitivity to a large number of allergens is determined by coating narrow bands of an elongated body of cellulosic material with a large number of separate identified allergens. The coated bands are separated from each other by narrow allergen-free bands. The cellulosic body is then contacted with blood serum of the patient, washed and contacted with an anti-immunoglobulin E (IgE) specific antiserum labeled with either a fluorescent material or a radioactive material. The cellulosic body is again washed and bands containing fluorescent material or radioactive material are identified.

5 Claims, 5 Drawing Figures

IN VITRO METHOD FOR DETERMINING ALLERGIC HYPERSENSITIVITY

BACKGROUND OF THE INVENTION

Approximately ten percent of all human beings can be designated allergic or atopic. They have become sufficiently hypersensitive to substances commonly present in the environment to experience significant symptoms on exposure to these substances. The majority suffer from readily identifiable allergic symptoms such as hayfever, asthma, eczema, hives and localized swellings. Regardless of symptoms the preferred methods of therapy are either to remove the patient from the substance to which he is sensitive or failing that, to treat the patient with increasing doses of the substance and thereby elevate his threshold for reaction. The allergic symptoms are induced by the presence of allergens in the substances to which the individuals are sensitive. An allergen may be defined by first defining an antigen which is a substance that can stimulate the production of antibody in an animal, the produced antibody is specifically reactive with the antigen. An allergen is a special antigen which stimulates a synthesis of a class of antibody which causes allergy. Before either of the methods of therapy noted above can be applied it is necessary to identify the allergen. Currently, allergic hypersensitivity is determined by direct skin tests on patients. In the skin tests minute quantities of various allergens are injected into or under the skin, visible but usually readily tolerated lesions will appear on the skin of the patient at the point of injection of an allergen to which the patient is hypersensitive. The skin test has limitations. It does not work well in either the very young or the very old, there is some risk to the patient during skin testing and there are relatively few physicians expert in performing and interpreting skin tests so that the method cannot be made widely available and the method is a costly one. An in vitro system for assaying allergic hypersensitivity would be simpler, safer and cheaper than the skin test method. Such a system has not heretofore been available.

BRIEF SUMMARY OF THE INVENTION

Pursuant to the present invention hypersensitivity to a large number of allergens is determined in vitro by testing a small sample of the blood serum of the patient. Briefly the method consists in bonding a plurality of separate allergens to an elongated porous support body to form a series of narrow bands of bonded allergen separated by narrow bands of allergen-free support, then contacting the allergen bonded support with blood serum of the patient, then contacting the support with anti-immunoglobulin E specific antiserum labeled with either a fluorescent material or with a radioactive material, washing the support to remove unreacted immunoglobulin E antiserum and then identifying those bands containing the fluorescent or radioactive material. The presence of either fluorescent material or radioactive material on a particular band indicates that the allergen initially placed on that band is an allergen to which the patient is hypersensitive.

DETAILED DESCRIPTION OF THE INVENTION

The appended drawings illustrate two methods of preparing bodies of cellulosic material having narrow bands of separate identified allergens distributed along the length of the body of material.

Figure 2:
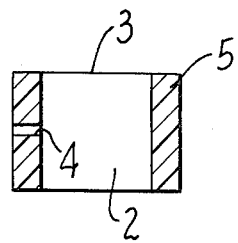
FIG. 2 is a lateral cross section of a jig taken through A—A of FIG. 1.
Figure 1:
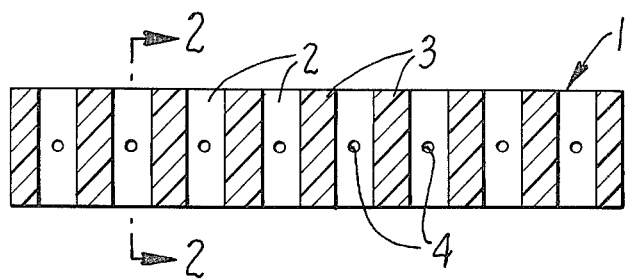
FIG. 1 is a cross section of a jig arrangement used to impregnate a strip of cellulosic paper with narrow bands of allergen.
Figure 3:
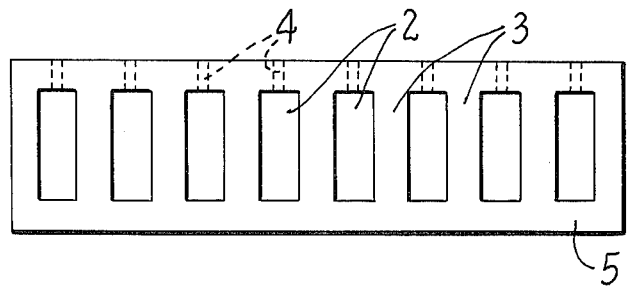
FIG. 3 is a plan view of the jig device.
Figure 4:
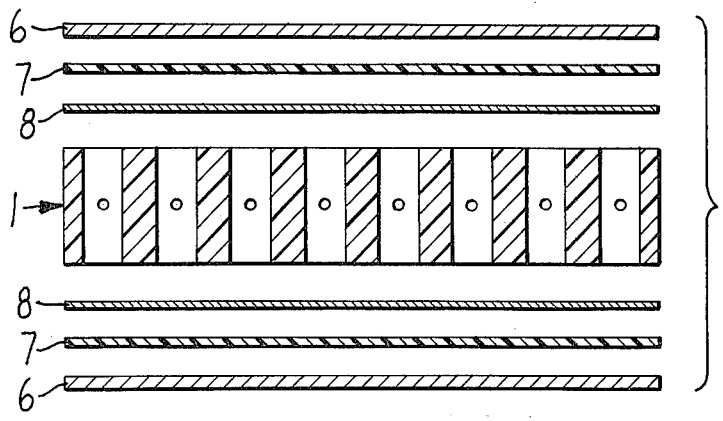
FIG. 4 is an expanded longitudinal cross section of the jig arrangement showing the assembly of parts used in impregnating the cellulosic paper with narrow bands of various allergenic materials.

Referring now to FIG. 1, the body 1 of the jig may be fabricated from glass or metal. Reservoirs 2 are open spaces within the body of the jig adapted to receive the allergen solutions. The open reservoirs are separated by solid sections 3 so that along the length of the jig there are series of alternate open and solid sections. Apertures 4 are openings into the reservoirs to permit the introduction of the allergen solutions. The reservoirs 2 are open at top and bottom of the jig. The jig assembly prior to introduction of the allergen solutions is shown in FIG. 4. Strips of paper 8 are laid across top and bottom of jig, over the strips of paper are laid thin sheets of styrofoam or foamed rubber 7 and over the styrofoam or rubber are laid solid metal plates 6. These materials are clamped together so that the paper is held securely across the top of the jig compressed by the porous material 7 and held by steel plates 6. After the assembly is clamped separate identified allergens are injected into each of the reservoirs through apertures 4 until the reservoirs are completely filled and the allergenic solutions are in contact with the paper at top and bottom of jig. After the reservoirs are filled the apertures 4 are closed.

Prior to assembling the jig arrangement shown in FIG. 4 the paper strips 8 are impregnated with a cyanogen halide.

If desired, a control comparison can be made by filling a few of the reservoirs with a material other than an allergen, i.e., distilled water or a dilute solution of animal protein, the animal being a specie other than the specie from which the serums used in the method are obtained.

Figure 5:
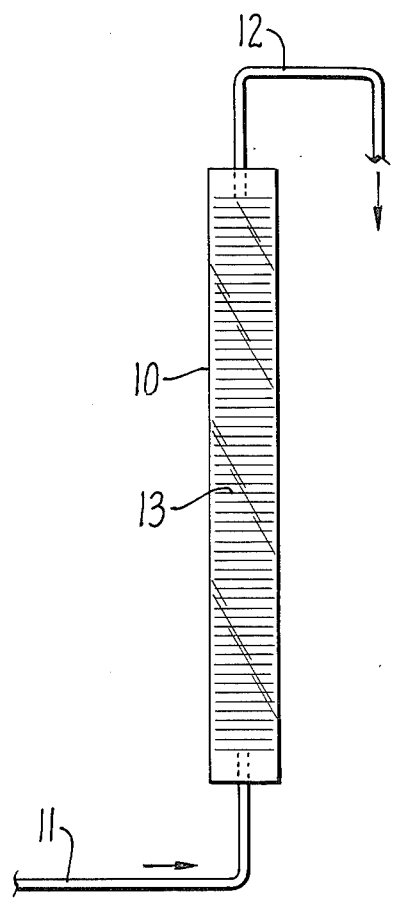
FIG. 5 is a front view of an alternate arrangement for producing a plurality of narrow bands of cellulose impregnated with various allergens in a columnar arrangement.

FIG. 5 illustrates an alternate arrangement of an elongated cellulosic body in columnar form. Glass or metal column 10 if filled by introducing a thin layer of powdered cellulose impregnated with a cyanogen halide then a thin layer of unimpregnated cellulose, then a further layer of cyanogen halide impregnated cellulose and so on until the column is filled. Each layer of cyanogen halide impregnated cellulose is contacted with a solution of a specific identified allergen before it is placed in the column. After the column is filled it is sealed. Tube 11 is used for introduction of the several solutions used in the process into the column so that the solutions flow upwardly in the column contacting each of the layers of cellulose and after the column is filled the solution leaves the column through tube 12 which may be attached to the bottom of a second column, etc. Instead of packing the column with separate layers of allergen containing cellulose and allergen-free cellulose, cellulose containing each of the allergens can be compressed into wafers or sandwiched between two thin sheets of a porous or perforate film (mylar, nylon, etc.) and wafers having diameters approximating the diameter of the column diameter can be cut from the sheets and slid into the column to form a stack of wafers each having a different allergen bonded to the cellulose filling.

The several steps of the process using the jig arrangement shown in FIG. 1 to 4 are carried out as follows:

A. Cellulose paper strips 8 are impregnated with a cyanogen halide for instance cyanogen bromide.

B. The strips are firmly attached to top and bottom of the jig as illustrated in FIG. 4 and then each reservoir 2 is nearly filled with a separate identified allergen solution through apertures 4. After all of the reservoirs, typically about 150 have been filled each with a separate identified allergen the jig assembly is rotated for a number of hours at room temperature in order to insure adequate contact of the allergenic solutions with the paper strips. Apertures 4 are opened and reservoirs are washed out with dilute sodium bicarbonate solution or with water. The paper strips are then removed from the jig. Typically the strips are about 1 to 1.5 centimeters in width and the narrow bands along the length of the strips about ¼ cm in width and about 1 cm in length. These narrow bands are separated by allergen-free narrow bands which are in contact with solid sections 3 during the impregnation, which are also about ¼ cm in width.

C. After the paper strips are removed from the jig they are placed in a beaker and washed with an amine solution preferably a primary amine such as monoethanolamine or ethylamine and the like to deactivate and/or remove residual cyanogen halide which has not reacted with allergen solution. The washing is usually performed by sealing the beaker and agitating it for a time sufficient to obtain thorough deactivation and/or removal of the cyanogen halide. Typically, contact of the amine with the strip for a period of about 3 hours is found adequate for complete cyanogen halide deactivation or removal. After contact with the amine the strips are thoroughly washed to remove any residual amine from the paper strips. Washing can be carried out with distilled water, preferably with dilute i.e., 0.1 molar sodium bicarbonate. The washing must be adequate to accomplish complete removal of unreacted amine from the paper strips. Most desirably, especially if the strips are to be stored before use, they are first washed with dilute sodium bicarbonate then with buffer A, then with buffer B and then they can be stored indefinitely in a body of buffer B at temperatures − 40 C. or below. Buffer A is a 1/10 molar acetate buffer having a pH about 4.0 A 100 cc lot of buffer A can be prepared by mixing together 41 millimeters of 0.2 molar acetic acid, 9 millimeters of 0.2 molar sodium acetate, and 50 milliliters of distilled water. Buffer B is a phosphate buffered saline solution having a pH about 7.5. About 1 liter of buffer B can be prepared by mixing together 500 milliliters of 0.1 molar phosphate buffer, 500 milliliters of a 0.9 wt. % sodium chloride solution, 10 milliliters of 5 wt. % sodium azide solution and 3 grams of human serum albumin.

D. Paper strips prepared as above can be used immediately or after long periods of storage as desired. To use a stored strip, the strip is first thawed then coiled and placed in a vial with 1 milliliter of the patient's blood serum diluted 2 to 3 with distilled water or preferably with buffer B. The vial is then stoppered and agitated for a number of hours at room temperature.

E. After several hours agitation the strip is thoroughly washed with a dilute solution of albumin, preferably with a slightly alkaline buffered solution of albumin such as buffer B or buffer C. Buffer C is of the same composition as buffer B noted above, but contains in addition a small amount about 1% of a surface active agent preferably a nonionic surfactant such as a polyglycol ether of an alkyl phenol or of a fatty alcohol, for example, polyoxyethylene, sorbitan, monolaureate sold by Atlas Chemical Company under the name "Tween-20" is a representative suitable compound. While this washing step is preferably performed with buffer C, adequate washing can, as noted above, be accomplished with a dilute solution of an albumin and distilled water.

F. After residual serum has been washed from the strip, 1 milliliter of anti-immunoglobulin E (IgE) specific antiserum labeled with either a fluorscent material or a radioactive material is introduced into the vial containing the paper strip. Anti-immunoglobulin E specific antiserums from sheep or rabbits are commercially available. The commercial serums are desirably but not necessarily further purified for instance by an immunosorbent technique described by Robbins, Haimovich and Sela Immunochemistry, Vol. 4, p. 11 (1967). In this purification a bromoacetyl cellulose-IgE conjugate is used.

The anti-IgE in the serum is bound to the IgE conjugate and after washing is eluted with a 0.2 molar glycine-HC1 buffer, pH 2.2 containing 0.1% human serum albumin.

Preparations of IgE suitable for conjugation to bromoacetylcellulose can be obtained from either IgE myeloma serum or from sera obtained from patients with high levels of IgE because of chronic parasitic infestation. The IgE can be fractionated by column chromatography using a method already described. (Ishizaka, K., Ishizaka, T., and Terry W.D., J. Immumonlogy 99: 849, 1967).

The purified anti-IgE preparation is preferably passed through a column of cellulose-albumin conjugated fibers to further reduce the nonspecific adherence of labeled impurities in the test. The anti-IgE material is labeled with either a fluorescent material such as fluorescene isothyocyanate, rhodamine or hydrazine hydrochloride salicylaldehyde. A variety of fluorescent materials may be used to label the IgE, the only restriction being that the fluorscent material should not itself directly react with cellulose. Alternatively, the anti-IgE may be labeled with a mildly radioactive material such as iodine 125 which can be added in the form of a sodium iodide solution. While iodine 125 is excellently adapted for labeling the IgE serum, other radioactive materials having gamma energies in the range about 0.2 to 0.2 Mev, and half lives of 30 days or more (ease of storage) and which do not directly react with cellulose may be used. The labeling is accomplished by simply mixing the fluorescent material or the radioactive material with the anti-IgE. The method described by Coons (Int. Rev. Cytol) Vol. 5, p. 1 (1956) may be used to label the anti-IgE with a fluorescent material and the method described by Greenwood and Hunter (Nature) Vol. 194, p. 495 (1962), may be used to label the anti-IgE with iodine 125. The vial containing the paper strip and the labeled anti-IgE is agitated for several hours at room temperature to permit reactions, if any, between the labeled anti-IgE and the patient's serum contained on the strip. The strips are then washed thoroughly with distilled water containing in solution a small amount of albumin or with buffer B of buffer C. The strips are then analyzed to determine which of the bands have retained either fluorscent material or radioactive material as the case may be.

$I^{125}$-labeled material can be quickly and efficiently identified by gamma-emission strip-scanning spectrometers which are commercially available and typically used for longitudinal scanning of paper electrophoresis strips.

Fluorscent labeled material can be read by exposing the entire strip to light of the exciting wavelength and simultaneously moving the strip across a narrow slit behind which a photocell is situated which is sensitive to the wavelength of light emitted by the label. Alternately, the strip can be placed before a photocell sensitive to the wavelength of emitted light and scanned by a laser whose light is of a wavelength which is appropriate for excitation of the label.

When a particular band on the strip is noted to be either fluorescent or radioactive it is then known the patient is hypersensitive to that allergen which was contacted with that band of the strip of paper.

When, pursuant to the method described above, the allergens to which a patient is hypersensitive have been identified and the patient has been treated for the allergy by hyposensitization injections and it is desired to determine the efficacy of the therapy, the method above described can be modified to make such determination. To make this determination an anti-immunoglobulin G (IgG) specific antiserum labeled either with a fluorescent material or a radioactive material is used in step F of the procedure instead of the anti-IgE specific antiserum. The anti-IgG will detect IgG type antibodies the presence of which will indicate effectiveness of the therapy applied. Determination that IgG type antibodies in the blood serum are increasing and that IgE type antibodies are simultaneously decreasing is a solid indication of therapy effectiveness.

Substitution of anti-IgG for anti-IgE in step F can also be used to permit the determination of the degree of immunity of the patient to organisms such as those of tetanus, diphtheria, and rubella. In making these determinations, of course, extracts of these organisms are contacted with the paper strips in step B instead of the allergen solutions used when hypersensitivity is being determined.

I claim:

1. The method of determining hypersensitivity of human patients to allergens which comprises coating an elongated body of cellulose material with a cyanogen halide, coating a plurality of narrow bands of the cellulosic body with separate identified allergens said bands being separated from each other by narrow allergen-free bands, washing the cellulosic body with an amine to remove any unreacted cyanogen halide, contacting the washed cellulosic body with the blood serum of the patient, washing the cellulosic body with a dilute aqueous solution of albumin to remove any blood serum not bonded to the cellulosic body, contacting the cellulosic body with an anti-immunoglobulin E serum labeled with a fluorscent material or with a radioactive material, washing the cellulose body with a dilute aqueous albumin solution to remove any unbonded anti-immunoglobulin E serum and then identifying those narrow bands previously contacted with allergen which contain fluorescent material or radioactive material.

2. The method of determining hypersensitivity of human patients to allergens which comprises:
   a. coating an elongated body of cellulosic material with a cyanogen halide,
   b. coating a plurality of narrow bands of the cyanogen halide coated cellulosic body with separate identified allergens, said narrow bands being separated from each other by narrow allergen-free bands,
   c. washing the cellulosic body with an amine to remove unreacted cyanogen halide,
   d. washing the cellulose body to remove residual amine,
   e. contacting the washed cellulosic body with blood serum of the patient,
   f. washing the cellulosic body with a dilute solution of an albumin,
   g. contacting the cellulosic body with an anti-immunoglobulin E specific antiserum labeled with a cellulose inert fluorescent material or with a cellulose inert radioactive material,
   h. washing the cellulosic body with a dilute solution of an albumin to remove unbonded fluorescent material or radioactive material, and
   i. identifying those narrow bands contacted with allergen in step (b) which contain fluorescent or radioactive material.

3. A strip of paper impregnated with narrow bands of separate identified allergens for use in in vitro determination of hypersensitivity of human patients to allergens, said strip consisting essentially of the paper itself and narrow bands of allergens bonded to the paper by a cyanogen halide, the bands being spaced apart and separated by narrow allergen-free bands.

4. The article defined in claim 3 wherein the strip of paper is also impregnated at intervals with narrow bands of albumin said bands being spaced along the strip of paper so that there is at least one albumin impregnated band for each fifteen allergen bands.

5. A strip of paper as defined in claim 3 prepared bu impregnating the entire strip with a cyanogen halide, contacting a plurality spaced apart narrow bands on said strip with solutions of separate identified allergens for several hours to cause binding of the allergens to the strip by the cyanogen halide, washing the strip with an amine to remove unreacted cyanogen halide and then washing the strip to remove any residual amine.

* * * * *